May 24, 1966 W. ZOMBORY ETAL Plant Pat. 2,631
DIANTHUS PLANT
Filed April 8, 1965
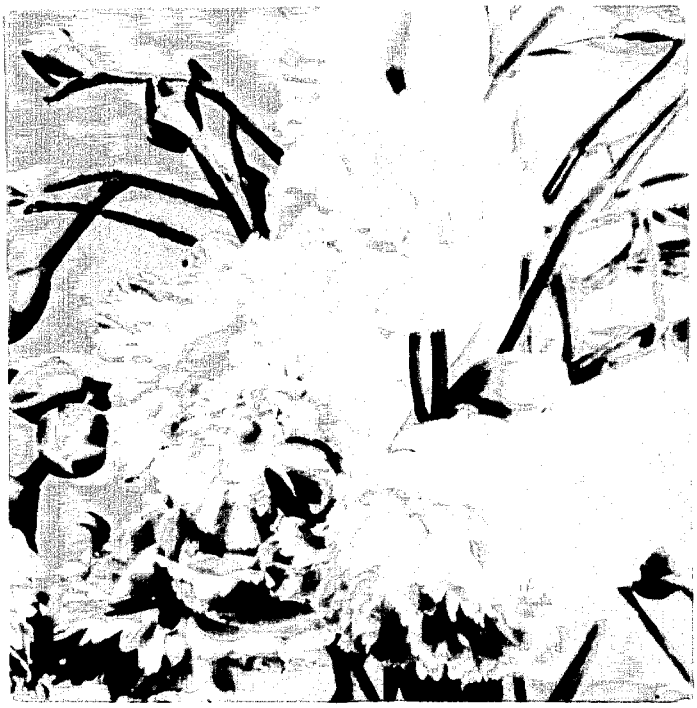
Inventors.
William Zombory and
Sophia B. Zombory
By: Robb & Robb
Attorneys.

United States Patent Office

Plant Pat. 2,631
Patented May 24, 1966

2,631
DIANTHUS PLANT

William Zombory and Sophia B. Zombory, Detroit, Mich., assignors to Jackson & Perkins Company, Newark, N.Y., a corporation of New York Filed Apr. 8, 1965, Ser. No. 446,753
1 Claim. (Cl. Plt.—72)

The present invention relates to a new and distinct variety of dianthus plant, which was originated by us by crossing an unnamed and unpatented large, pink-flowered variety of the species botanically known as "Dianthus allwoodi" (unpatented) with an unnamed and unpatented white flowered seedling of the variety known as "Dianthus Caprice" (Plant Patent No. 1,851).

The primary objective of this breeding was to produce a new and improved dianthus variety having an ever-blooming habit, compact form and bearing red colored flowers. This objective was fully achieved, along with other desirable improvements, as evidenced by the following unique combination of characteristics which are outstanding in our new variety and which distinguish it from its parents, as well as from all other varieties of which we are aware:

(1) A compact habit of plant growth;

(2) An ever-blooming habit, with the blooms beginning the first year when grown from cuttings;

(3) A more compact flower habit than other dianthus seedlings;

(4) Flower petals having lightly scalloped edges;

(5) A distinctive and attractive general color tonality of the flowers corresponding to Spinel Red, lightly overcast with Rose Color; and (6) A strong flower fragrance corresponding to Old Spice.

Asexual reproduction of our new variety by cuttings, as performed at Detroit, Michigan, and also at Newark, New York, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with Ridgway's Color Standards and Nomenclature:

Parentage: Seedling.

*Seed parent.*—An unnamed, large, pink-flowered variety of the species botanically known as "Dianthus allwoodi."

*Pollen parent.*—"Dianthus Caprice."

Blooming season: Starts blooming the first year when grown from cuttings, with blooms occurring during June and July and again during September and October.

*Plant*

Growth: Medium tall (about 12½ inches); compact.

Leaves: Many bottom leaves in tufts; about 5 inches long; narrow; thick. Color—Bice Green, Plate 17, with silvery sheen of Mytho Green, Plate 41.

Flower stems: About 12 inches long; strong. Color—Bice Green, Plate 17.

*Flower*

Borne: From 1 to 3 flowers per stem; borne mostly on own branched stalks, but some of the laterals nearly sessile.

Form: Compact; edges of petals lightly scalloped.

Size: About 2½ inches in diameter, with later flowers on laterals measuring about 1¼ inches in diameter.

Petals: Average from 30 to 35; about ¾ inch wide; about 1 inch long; small blotch of White color, Plate 53 at beginning of throat. Color: Upper side—Spinel Red, Plate 26, lightly overcast with Rose Color, Plate 12; reverse side—Tyrian Rose, Plate 12, lightly overcast with Spinel Pink, Plate 26; claw—White, Plate 53, blended with Glass Green, Plate 31.

Calyx: Cylindrical; teeth about ½ inch long; erect; splits on wide open flower. Color—teeth of Cress Green, Plate 31, with lower half of calyx very lightly overcast with Garnet Brown, Plate 1.

Bracts: 4 in number; small. Color—Cress Green, Plate 31 at tip, with lower part of bract Absinthe Green, Plate 31.

Stamens: From 6 to 8 in number. Color—White, Plate 53.

Anthers: Color—Pale Mauve, Plate 25.

Ovary: Small, oval.

Fragrance: Strong. Nature—Old Spice.

We claim:

A new and distinct variety of dianthus plant, substantially as herein shown and described, characterized particularly as to novelty by the unique combination of a compact habit of plant growth, an ever-blooming habit, with the blooms beginning the first year when grown from cuttings, a more compact flower habit than other dianthus seedlings, flower petals having lightly scalloped edges, a distinctive and attractive general color tonality of the flowers corresponding to Spinel Red, lightly overcast with Rose Color, and a strong flower fragrance corresponding to Old Spice.

No references cited.

ABRAHAM G. STONE, *Primary Examiner.*